United States Patent [19]

Schmidt et al.

[11] Patent Number: 4,474,597
[45] Date of Patent: Oct. 2, 1984

[54] AGENT FOR SELECTIVELY COMBATING WEEDS IN RICE

[75] Inventors: Robert R. Schmidt, Bergisch-Gladbach; Heinz Förster, Wuppertal, both of Fed. Rep. of Germany

[73] Assignee: Bayer Aktiengesellschaft, Leverkusen, Fed. Rep. of Germany

[21] Appl. No.: 461,290

[22] Filed: Jan. 27, 1983

[30] Foreign Application Priority Data

Feb. 16, 1982 [DE] Fed. Rep. of Germany ....... 3205400

[51] Int. Cl.$^3$ ............................................ A01N 43/34
[52] U.S. Cl. ............................................ 71/90; 71/88
[58] Field of Search ...................................... 71/88, 90

[56] References Cited

U.S. PATENT DOCUMENTS 3,198,786  8/1965  Tilles et al. ............................ 71/88
4,220,467  9/1980  Dombay et al. ........................ 71/93

FOREIGN PATENT DOCUMENTS 5501     11/1981  European Pat. Off. ............... 71/90
2822155  11/1979  Fed. Rep. of Germany.
53-47530  4/1978  Japan .................................... 71/93
158702   12/1981  Japan .................................... 71/93

OTHER PUBLICATIONS

Chemie der Pflanzenschutz- und Schädlings-bekämpfungsmittel, vol. 5, 1977, p. 93.

Primary Examiner—Catherine L. Mills
Attorney, Agent, or Firm—Sprung Horn Kramer & Woods

[57] ABSTRACT

A herbicidal composition containing a synergistic combination of active ingredients which are (1) 2-(2'-benzothiazolyloxy)-N-methyl-N-phenyl-acetamide and (2) molinate alone or in admixture with a solid or liquid diluent or carrier, has high herbicidal activity and is especially suitable for use as a selective herbicide against weeds in rice crops.

4 Claims, No Drawings

AGENT FOR SELECTIVELY COMBATING WEEDS IN RICE

The present invention relates to a new herbicidal synergistic active compound combination of a certain oxyacetamide on the one hand and a certain thiolcarbamate.

The new herbicidal compositions have a particularly good herbicidal activity, in particular for selectively combating weeds in rice.

It has already been disclosed that 2-(2'-benzothiazolyloxy)-N-methyl-N-phenyl-acetamide [2-benzothiazolyloxyacetic acid N-methylanilide] can be used as a herbicide (see DE-OS (German Published Specification) No. 2,822,155; and European Pat. No. 0,005,501).

It has also been disclosed that S-ethyl hexahydro-1H-azepine-1-carbothioate (molinate) can be employed for combating weeds in rice (see R. Wegler, Chemie der Pflanzenschutz- und Schädlingsbekämpfungsmittel (Chemistry of plant protection agents and pest-combating agents), Springer Verlag Berline, Heidelberg, New York, volume 5-Herbicides, page 93, (1977)).

However, the action of both abovementioned, known herbicides against certain important graminaceous weeds, for example Echinochloa crus galli, is not always satisfactory when low dosages are used.

The present invention now provides a new herbicidal composition containing as active ingredients (1) 2-(2'-benzothiazolyloxy)-N-methyl-N-phenylacetamide of the formula

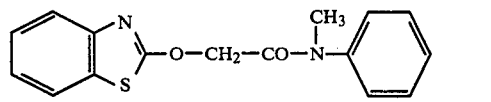

and (2) S-ethyl hexahydro-1H-azepine-1-carbothioate (molinate) of the formula

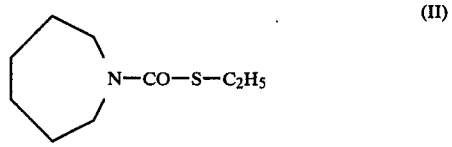

alone or in admixture with a solid or liquid diluent or carrier.

The composition of the invention has a particularly high herbicidal activity, without damaging rice crops.

Surprisingly, the combination according to the invention has an activity with respect to weeds which is substantially higher than the sum of the actions of the individual active compounds. An unforeseeable genuine synergistic effect, and not just an additive action, is present. The active compound combination thus represents a valuable enrichment of selective rice herbicides.

The active compounds as such, which are present in the active compound combination according to the invention, are already known (see DE-OS (German Published Specification) No. 2,822,155 and U.S. Pat. No. 3,198,786).

The synergistic effect of the active compound combination according to the invention is particularly pronounced at certain concentration ratios. However, the weight ratio of the active ingredients in the composition can be varied within a relatively wide range. In general, 0.1 to 10 parts by weight, preferably 0.2 to 5 parts by weight, of active ingredient (2) are employed per part by weight of active ingredient (1).

The following may be mentioned as examples of weeds which in general occur in rice crops and may definitely be combated using the active compound combination according to the invention:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

However, the use of the active compound combination according to the invention is in no way restricted to these genera, but also extends in the same manner to other plants.

The certain action of the new active compound combination even against Panicum-like weeds, such as, in particular, Echinochloa crus galli, and its very good toleration by rice (Oryza sativa) should once again be especially singled out. Its use as a selective rice herbicide is therefore particularly to be recommended.

The active compound combination according to the invention can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain 0.1 to 95 percent by weight of total active compounds, preferably from 0.5 to 90 percent by weight.

The active compound combination according to the invention is used in general in the form of finished formulations. However, the active compounds present in the active compound combination can also be mixed, as individual formulations, during use, that is to say they may be used in the form of tank mixtures.

The new active compound combination, as such or in the form of its formulations, can also be used as a mixture with other known rice herbicides, finished formulations or tank mixing again being possible. Mixtures with other known active compounds, such as fungicides, insecticides, acaricides, nematicides, bird repellents, growth factors, plant nutrients and agents which improve soil structure, are also possible.

The new active compound combination can be used as such, in the form of its formulations or in the use forms prepared therefrom by further dilution, such as ready-to-use solutions, suspensions, emulsions, powders, pastes and granules. They are used in the customary manner, for example by watering, spraying, atomizing, dusting or scattering.

The use amounts of the active ingredients of compositions according to the invention can be varied within a certain range; they depend, inter alia, on the weather and on the soil factors. In general, the amounts used are between 0.1 and 10 kg of total active ingredients per ha, preferably between 0.2 and 5 kg/ha.

The compositions according to the invention can be applied either before or after emergence of the plants.

The present invention also provides a method of combating weeds which comprises applying to the weeds, or to a habitat thereof, a composition of the present invention.

The present invention further provides crops, especially rice, protected from damage by weeds by being grown in areas in which immediately prior to and/or during the time of the growing a composition of the present invention was applied.

It will be seen that the usual methods of providing a harvested crop may be improved by the present invention.

The good herbicidal action of the new active compound combination can be seen from the examples which follow.

Whereas the individual active compounds exhibit weaknesses in their herbicidal action, the combination shows a very broad action against weeds, which goes beyond a simple summation of the actions.

A synergistic effect is involved in herbicides whenever the herbicidal action of the active compound combination is greater than that of the individually applied active compounds.

The action to be expected for a given combination of two herbicides can be calculated as follows (see S. R. Colby, "Calculating synergistic and antagonistic responses of herbicide combinations", Weeds 15, pages 20-22 (1967):

If $X = \%$ damage by herbicide A when using p kg/ha and $Y = \%$ damage by herbicide B when using q kg/ha and $E =$ expected damage by herbicides A and B when using p and q kg/ha, then $E = X + Y - (X \cdot Y)/100$ If the actual damage is greater than calculated, the action of the combination is super-additive, that is to say a synergistic effect is concerned.

In the following examples, it is shown that the found herbicidal action of the active-compound combination according to the invention on the weeds is greater than the calculated action, that is to say a genuine synergistic effect is concerned.

EXAMPLE A

Water rice test

To produce a suitable use form of the active compound combination according to the invention, the active ingredient (1) was employed in the form of a conventional 70% strength wettable powder and the active ingredient (2) was employed in the form of the commercial 70% strength emulsion concentrate (Trade Mark "HYDRAM", from Stauffer & Co.). For this purpose, both preparations were mixed in the mixing ratios given in the table, and the mixture was diluted with water; the concentration of the spray liquor was chosen so that the amounts of active compound given in the table were applied in 500 liters of water/ha.

Soil was introduced (to a depth of 5 cm) into 10 cm deep plastic dishes. Rice (Oryza sativa, "Kinmaze" variety) which had grown to a height of approx. 10 cm was planted in the soil. In addition, seeds of *Echinochloa crus galli* were sown. The soil was then placed under 3 to 4 cm of water. One day later, the active compound combination according to the invention, in the form of the spray liquor described above was applied by means of a spray nozzle, onto the dishes treated in this manner.

3 weeks after the application of the active compound, the growth of the plants was assessed visually in comparison with untreated control plants.

0% denoted no action (growth like untreated control).

100% denoted total destruction.

Active compounds, amounts used and results can be seen from Table A which follows.

TABLE A

Synergistic herbicidal action and toleration of the active compound combination (I) + (II)/water rice test

| Active compound or active compound combination | Amount used kg/ha | Echinochloa crus galli found* | Echinochloa crus galli calc.* | Rice (Oryza sativa) found* | Rice (Oryza sativa) calc.* |
|---|---|---|---|---|---|
| (I) known | 0.3 | 80 | | 0 | |
| (II) known | 0.3 | 15 | | 0 | |
| | 0.6 | 70 | | 0 | |
| (I) + (II) according to the invention | 0.3 + 0.3 = 0.6 | 99 | 83 | 0 | 0 |
| | 0.3 + 0.6 = 0.9 | 100 | 94 | 0 | 0 |

(I) = 2-(2′-Benzothiazolyloxy)-N—methyl-N—phenyl-acetamide
(II) = molinate
found* = damage (in percent) found
calc.* = damage (in percent) calculated according to the COLBY formula.

It is understood that the specification and examples are illustrative but not limitative of the present invention and that other embodiments within the spirit and scope of the invention will suggest themselves to those skilled in the art.

We claim:

1. A herbicidal composition consisting essentially of a herbicidally effective amount of (I) 2-(2′-benzothiazolyloxy)-N-methyl-N-phenylacetamide of the formula

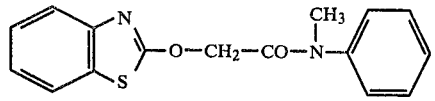

(II) about 0.1 to 10 times its weight of S-ethyl hexahydro-1H-azepine-1-carbothioate (molinate) of the formula

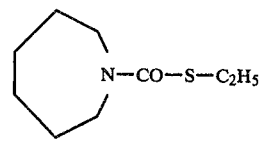

2. A herbicidal composition according to claim 1, wherein the weight ratio of I:II is from about 1:0.2 to 1:5.

3. A method of combating weeds, comprising applying to the weeds, or to a habitat thereof, a herbicidally effective amount of a composition according to claim 1.

4. In the growing of rice wherein a selective herbicide is applied to kill the weeds but not the rice, the improvement which comprises employing as the herbicide a composition according to claim 3 at a rate of about 0.1 kg per hectare up to an amount which will not kill the rice.

* * * * *